(12) United States Patent
Heppe et al.

(10) Patent No.: US 10,314,964 B2
(45) Date of Patent: Jun. 11, 2019

(54) STERILE TUBE COVERING FOR A MEDICAL TUBING SYSTEM

(71) Applicant: FRESENIUS MEDICAL CARE DEUTSCHLAND GMBH, Bad Homburg (DE)

(72) Inventors: John Heppe, St. Wendel (DE); Michael-Paul Jestram, Wetzlar (DE); Axel Kort, Mestlin (DE); Maria Millan-Galante, Bad Homburg (DE); Alexander Schrörs, Frankfurt (DE); Andreas Wüpper, Büttelborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 341 days.

(21) Appl. No.: 14/907,482

(22) PCT Filed: Jul. 18, 2014

(86) PCT No.: PCT/EP2014/065564
§ 371 (c)(1),
(2) Date: Jan. 25, 2016

(87) PCT Pub. No.: WO2015/011065
PCT Pub. Date: Jan. 29, 2015

(65) Prior Publication Data
US 2016/0166756 A1  Jun. 16, 2016

(30) Foreign Application Priority Data
Jul. 25, 2013 (DE) .......... 10 2013 012 365

(51) Int. Cl.
*A61M 1/36* (2006.01)
*A61M 39/08* (2006.01)
(Continued)

(52) U.S. Cl.
CPC ........ *A61M 1/3656* (2014.02); *A61M 39/165* (2013.01); *A61M 2039/087* (2013.01);
(Continued)

(58) Field of Classification Search
CPC .................. A61M 1/3656; A61M 39/165
(Continued)

(56) References Cited

U.S. PATENT DOCUMENTS 3,918,446 A * 11/1975 Buttaravoli .......... A61M 25/02
128/DIG. 26
4,340,052 A  7/1982 Dennehey
(Continued)

FOREIGN PATENT DOCUMENTS

CN  102811753 A  12/2012
DE  9112145 U1  1/1992
(Continued)

OTHER PUBLICATIONS

"Hygienemassnahmen bei Injelctionin, Punktionen, Infusionnen und bei praeoperativer Hautantiseptik [Sanitary measures for injections, punctures, infusions, and pre-operative skin antisepsis]," vol. 10, No. 1, Hygieneplan: Injektionen/Fusionen, Universitatsklinikum Tubingen (2005) 10 pages. [English translation of title and paragraph headings only].
(Continued)

*Primary Examiner* — Phillip A Gray
(74) *Attorney, Agent, or Firm* — Kilyk & Bowersox, P.L.L.C.

(57) ABSTRACT

The present invention relates to a tube covering for a tubing system, especially for monitoring a vascular access for an extracorporeal blood treatment. The inventive tube covering has at least one flexible bottom layer on which a section of the at least one tubing and/or a connection system of at least one tubing may be placed and has at least one flexible top
(Continued)

layer for covering the section of the at least one tubing and/or the connection system of the at least one tubing. The bottom layer and the top layer are joined to one another such that they form an openable wrapping for inserting the section of the at least one tubing and/or the connection system of the at least one tubing, fastening means for detachably joining the top layer and the bottom layer being provided on the top layer and bottom layer.

22 Claims, 11 Drawing Sheets

(51) Int. Cl.
    *A61M 39/10* (2006.01)
    *A61M 39/16* (2006.01)
(52) U.S. Cl.
    CPC ............... *A61M 2039/1005* (2013.01); *A61M 2039/1066* (2013.01); *A61M 2207/00* (2013.01)
(58) Field of Classification Search
    USPC ........................................................ 604/263
    See application file for complete search history.

(56) References Cited

U.S. PATENT DOCUMENTS

| 4,830,914 | A |   | 5/1989  | Vaillancourt |            |
|-----------|---|---|---------|--------------|------------|
| 4,965,554 | A | * | 10/1990 | Darling ................ | E04D 13/006 |
|           |   |   |         |              | 324/557    |
| 7,708,720 | B1| * | 5/2010  | Angstrom ............ | A61M 25/02 |
|           |   |   |         |              | 604/174    |
| 2010/0228231 | A1 |   | 9/2010 | Everett et al. | |
| 2013/0053754 | A1 |   | 2/2013 | Heppe | |

FOREIGN PATENT DOCUMENTS

| DE | 391 28 471 T2 | 7/1998 |
| DE | 10 2009 060 967 A1 | 6/2011 |
| WO | 98/56452 A1 | 12/1998 |
| WO | 1999024145 A1 | 5/1999 |
| WO | 2011028898 A1 | 3/2011 |
| WO | 2011289898 A1 | 3/2011 |
| WO | 2011116943 A1 | 9/2011 |
| WO | 2014008980 A1 | 1/2014 |

OTHER PUBLICATIONS

International Search Report from PCT/EP2014/065564, dated Oct. 9, 2014.

International Preliminary Report on Patenability in PCT/EP2014/065564, dated Feb. 4, 2016.

The State Intellectual Property Office of People's Republic of China Patent Office, Office Action for Chinese Patent Application No. CN201480041820.3 dated Jun. 12, 2018, with German-Language Translation.

* cited by examiner

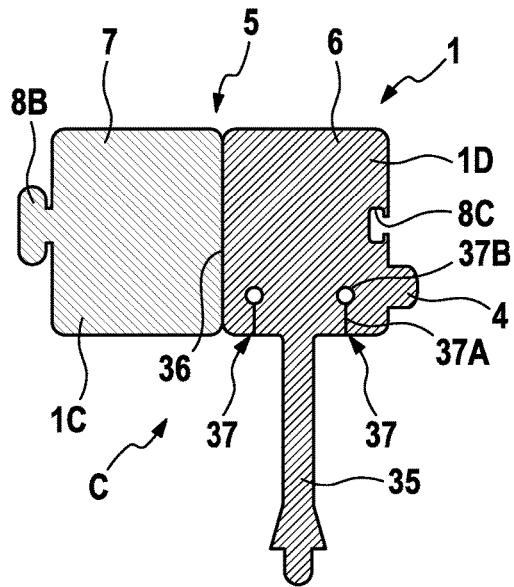
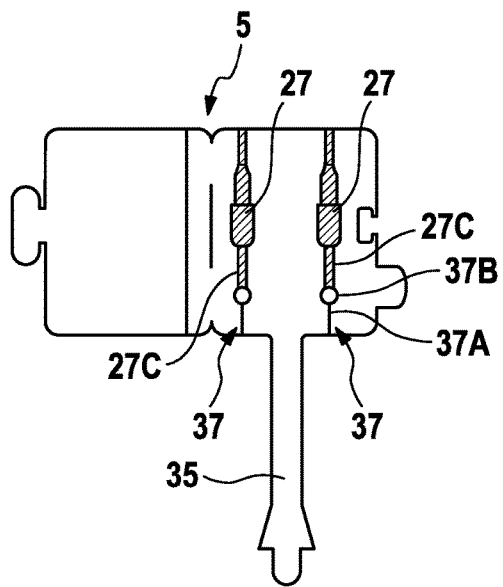
Fig. 3A  Fig. 3B
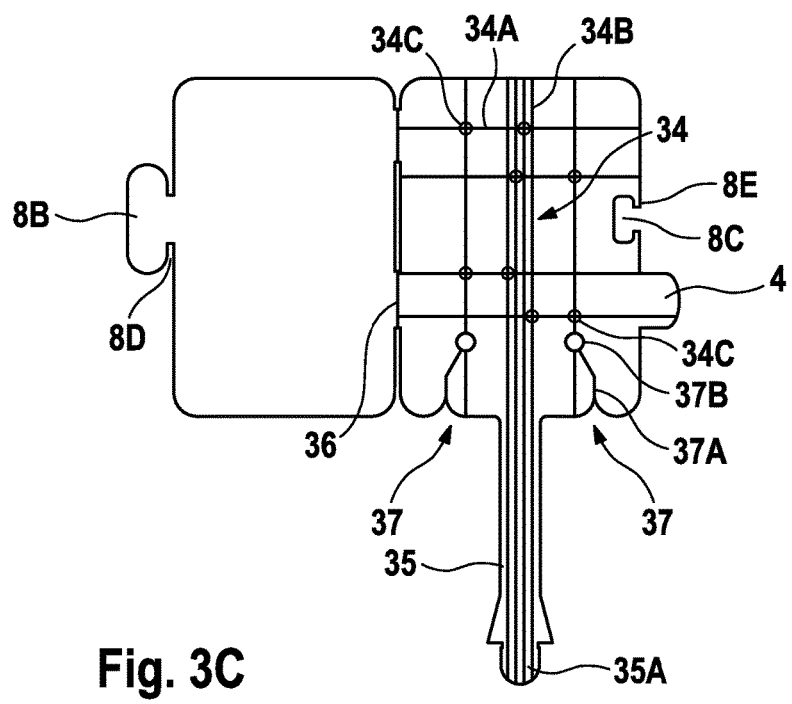
Fig. 3C

Fig. 6A
Fig. 6B
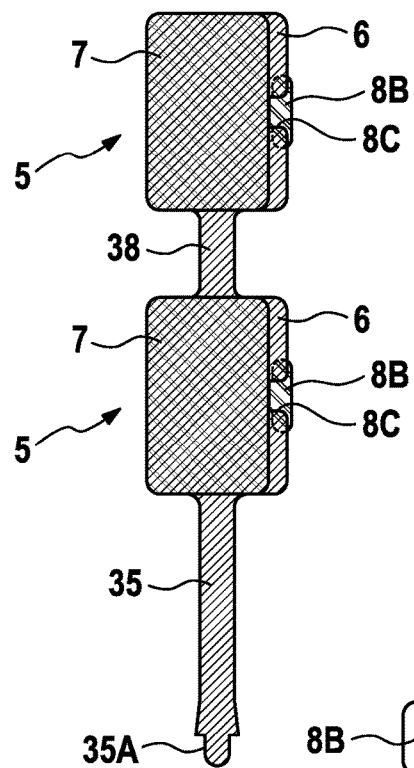
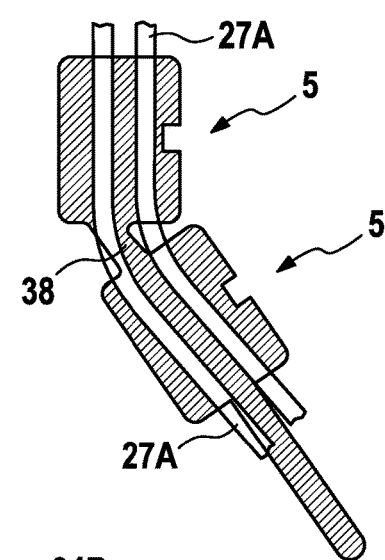
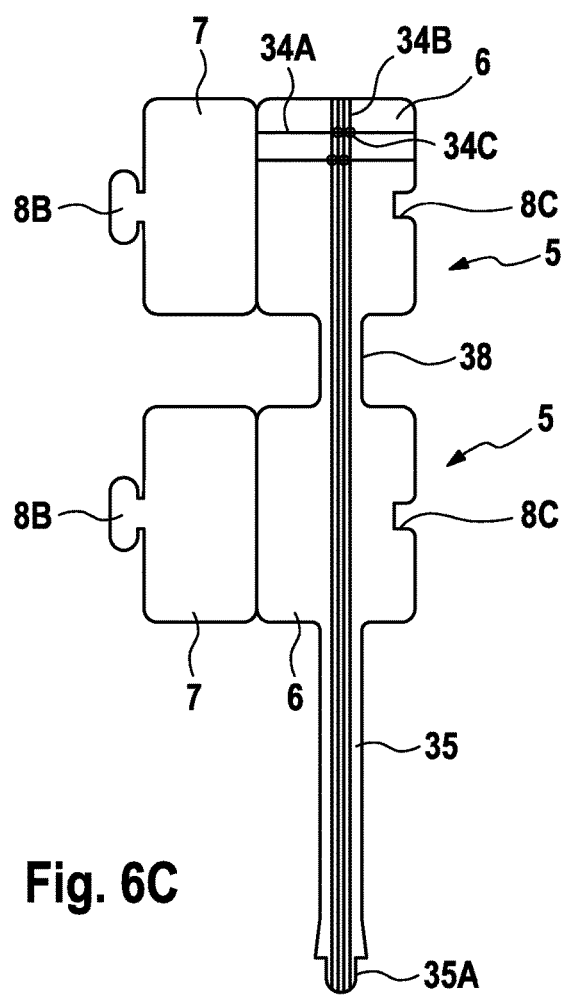
Fig. 6C

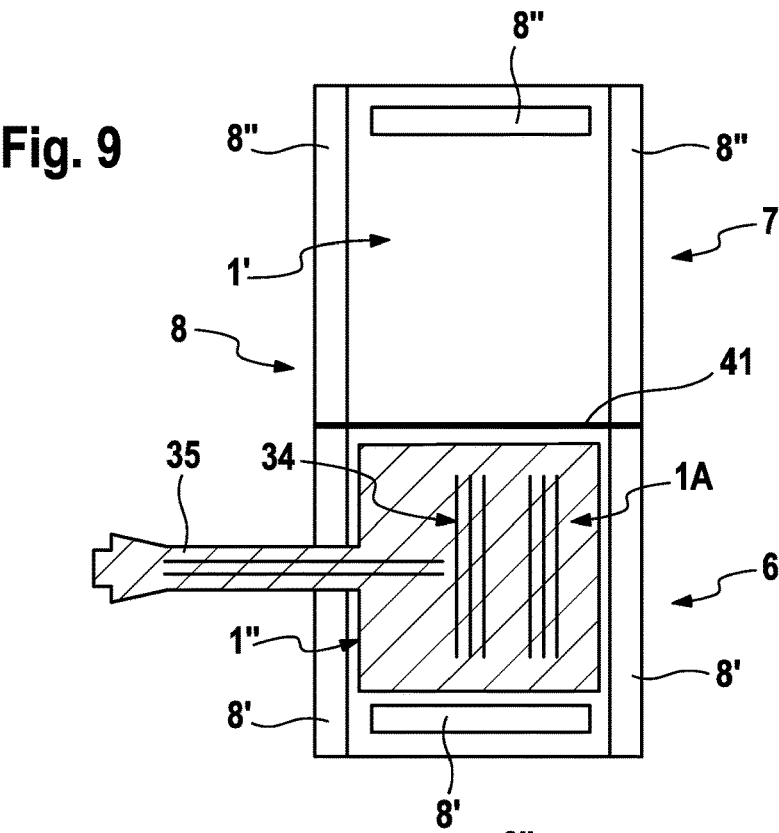
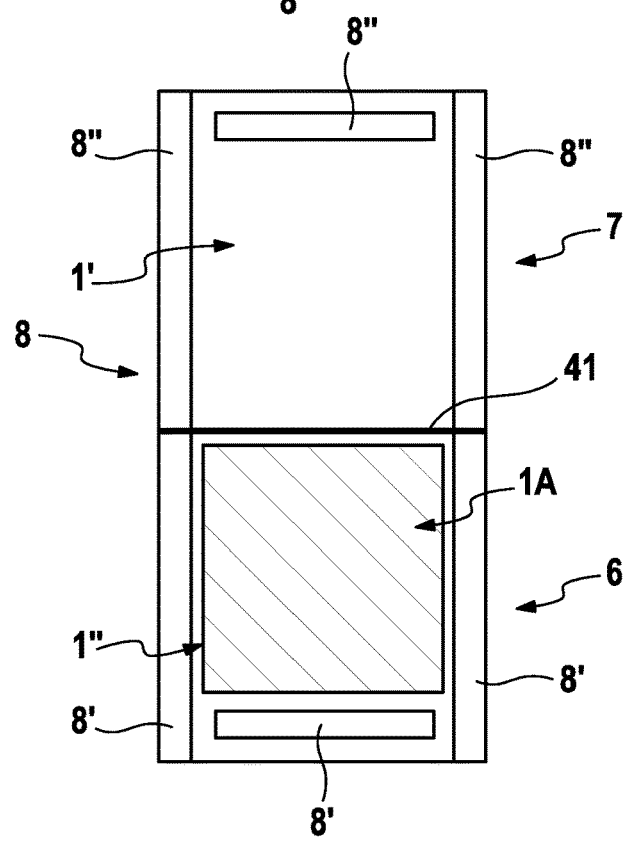

STERILE TUBE COVERING FOR A MEDICAL TUBING SYSTEM

CROSS REFERENCE TO RELATED APPLICATIONS

The present application is the national stage entry of International Patent Application No. PCT/EP2014/065564, filed on Jul. 18, 2014, the disclosure of which is expressly incorporated herein in its entirety by reference thereto, and claims priority to Application No. DE 10 2013 012 365.8, filed in the Federal Republic of Germany on Jul. 25, 2013.

FIELD OF INVENTION

The present invention relates to a sterile tube covering for a medical tubing system with which a fluid is supplied to a patient and/or a fluid is removed from a patient via tubing, especially for monitoring the vascular access during extracorporeal blood treatment, especially for monitoring a vascular access with a central venous catheter for acute or chronic dialysis.

BACKGROUND

In the field of medical technology various systems are known with which fluids may be removed from a patient or fluids may be supplied to a patient via tubing. In general access to the patients is with a catheter for inserting into body organs or with a cannula for puncturing blood vessels. During the examination or treatment proper access to the patient must be assured. Therefore it is necessary to monitor the patient access.

Extracorporeal blood treatment devices that involve in particular extracorporeal blood flow also require a proper access to the patient. Among known extracorporeal blood treatment devices are for instance dialysis systems and cell separators that require an access to the patient's vascular system. During extracorporeal blood treatment, blood is removed from the patient via arterial tubing with an arterial puncture cannula, and the blood is resupplied to the patient via venous tubing with a venous puncture cannula. During acute dialysis at intensive care stations, a central venous catheter is inserted in the neck or leg of the patient to create the vascular access. In the field of chronic dialysis, between 20% and 40% of patients have a catheter as a temporary or permanent vascular access.

In general luer connection systems are used for connecting and attaching tubing in the field of medicine; their connecting parts include an internal taper and an external taper. These connection systems are called luer lock connectors when the internal taper and external taper also include a thread for securing the connection. Although the luer lock connectors offer a very high level of reliability, in practice it has been found that when handled improperly, if there are material defects, or when used too frequently the connecting parts can detach from one another or microtears can occur in the material. US 2010/0228231 therefore suggests securing the connecting parts of a luer lock connector against unintentional detachment using an additional fixation of the connecting parts.

Various devices having different designs known for detecting blood escaping in general make use of the safety devices normally present in blood treatment devices; these initiate an immediate interruption in the extracorporeal blood flow if the vascular access is not in proper order.

Devices for detecting blood escaping at a puncture site are known that are embodied as a pad that comprises an absorbent material in which a moisture sensor is embedded. Such pads are known for instance from WO 2006/008866 A1, US 2005/0038325 A1 and U.S. Pat. No. 6,445,304 B1.

WO 99/24145 describes a device for detecting blood that has a rigid housing that can be closed with a cover and in which is arranged a moisture sensor. Passages are provided in the housing for feeding through the cannulas and tubing. It is a drawback that the housing with the moisture sensor is relatively costly to produce in large numbers and in practice is relatively difficult to handle. In addition, it is not possible to conduct a visual control because the sensors are positioned against the walls of the two halves of the housing.

SUMMARY

The underlying object of the present invention is to create a sterile tube covering for a tubing system that may be manufactured in large numbers in a cost effective manner. It is especially an object of the present invention to create a tube covering that may be manufactured in large numbers in a cost effective manner and that is for monitoring the vascular access during an extracorporeal blood treatment, especially for monitoring a vascular access with a central venous catheter for acute or chronic dialysis.

The inventive tube covering for a tubing system has at least one flexible bottom layer on which a section of at least one tubing and/or a connection system of at least one tubing may be placed and has at least one flexible top layer for covering the section of the at least one tubing and/or the connection system of the at least one tubing. The bottom layer and the top layer are joined to one another such that they form an openable wrapping for inserting the section of the at least one tubing and/or the connection system of the at least one tubing, fastening means for detachably joining the top layer and the bottom layer being provided on the top layer and bottom layer.

In this context a flexible layer shall be construed to mean a piece of material that is not rigid but rather is elastically deformable. The piece of material may be very flexible as a function of the material properties so that it can be easily adapted to the external conditions, or it may be less flexible.

The openable wrapping may be attached rapidly and securely, with no further aids, to a section of the tubing, especially in the area of the connection system for the tubing. In particular the wrapping may be attached simply in the area of a connection system, for instance a luer lock connection system, that connects a central venous catheter for acute dialysis to one or a plurality of tubings. Moreover, it is advantageous that the wrapping may be easily removed again from the tubing or the connection system during and/or after the treatment, which is particularly significant when using a central venous catheter.

Additional fastening means are not required for this. For instance, there is no need to fix the wrapping to the tubing or to the connector or to the skin of the patient with adhesive tape. This simplifies handling of the tube covering.

One particularly preferred embodiment provides that the top and bottom layers comprise two separate material pieces that are joined, in particular welded or glued, to one another on one side. If different materials are to be applied to the top layer and bottom layer, this results in manufacturing advantages, since the different materials may be applied to different material sheets independently of one another. From a manufacturing perspective it is advantageous if the different materials are first applied to the top layer and/or bottom layer and the top layer and/or bottom layer are not joined to one another until then.

One alternative embodiment provides that the tube covering is produced from a single material piece, of which one section is the top layer and one section is the bottom layer, the bottom side of the top layer lying on the top side of the bottom layer when the wrapping is folded closed. The openable wrapping therefore may be manufactured in large numbers from a single piece of material in a cost-effective manner using a single fold.

One superior aspect of the present invention is protecting the sterile tube covering for connection systems, especially a luer or luer-lock connector, from external influences, for instance penetration by microbes (splash guard). Thus the sterile cloth normally used in the past for covering the tube connection is no longer needed.

One special aspect of the present invention is the monitoring of a patient access, in particular a vascular access for an extracorporeal blood treatment, in particular a vascular access with a central venous catheter for acute or chronic dialysis.

For monitoring a patient access, in particular for escaping blood, one preferred embodiment of the inventive covering provides a moisture sensor with which an escaping fluid, especially blood, may be reliably detected. However, the patient access may also be monitored using a visual control if the top layer is transparent.

The tube covering may have both a moisture sensor and a transparent top layer so that in addition to detecting escaping blood with the moisture sensor, an additional visual control is also possible.

In one alternative embodiment, if the top layer is transparent the monitoring may be performed without a moisture sensor and exclusively using a visual control.

While an additional safeguard for a luer connector can only prevent the connector from coming apart, the inventive tube covering also permits detection of slow blood loss, for instance due to handling errors or material defects in the tube connection.

In one preferred embodiment, the bottom layer has an absorbent material for absorbing fluid that escapes from the connector.

One preferred embodiment provides that the bottom layer is a composite material made of an absorbent, preferably textile material, and a film, the film being arranged on the exterior side of the tube covering and the absorbent material being arranged on the interior side of the tube covering. In the embodiment with the moisture sensor, the absorbent material ensures that blood escaping at the tube connection point immediately travels to the moisture sensor. This increases the device's sensitivity overall. Consequently a potentially more cost-effective sensor may be used with a design-related lower sensitivity. The film covering the absorbent material prevents blood from a wound or due to a leak in the tubing system outside of the tube covering and sweat from the patient's skin from traveling from the exterior to the moisture sensor, so that false alarms are prevented.

If the film in the top layer is transparent, escaping blood may easily be seen using a visual control, especially if the absorbent material is a material in a light color, for instance a white material. In tests there was a pronounced enlargement of the site stained with blood.

The moisture sensor is preferably an electrical moisture sensor that has an electrically conducting structure. The electrically conducting structure of the moisture sensor is preferably embedded in the absorbent layer for fluids or is applied to the absorbent layer. The electrically conducting structure does not have to extend across the entire surface of the absorbent layer, since due to the absorbency of the layer detection of fluid in a section of the area is adequate.

The electrically conducting structure may have one or a plurality of conductors that extend in a plurality of sections across at least a part of the bottom layer. It may also be provided on the top layer.

In one particularly preferred embodiment, the absorbent material for embedding the electrically conducting structure is a textile material. The textile material is preferably a woven fabric having non-conducting warp threads and non-conducting weft threads as well as conducting warp threads and conducting weft threads that are arranged such that the electrically conducting structure is embodied in the woven fabric. The tube covering may thus be produced in large numbers in a particularly cost-effective manner in a weaving process without major production engineering complexity. It may also be cut out and sterilized without a great deal of technical complexity and may be provided as a sterile disposable sensor in suitable packaging. Such a woven fabric having an electrically conducting structure is described in detail in WO 2011/116943.

For the electrical contacting of the moisture sensor, the tube covering has connecting contacts that are embodied at the end of a longitudinal section of the tube covering, which section is connected to the top layer or bottom layer. What this attains is that the connecting contacts are spatially separated from the moisture sensor. Therefore, the area of the electrical contacting does not have to be sterile, in contrast the area in which the moisture sensor is disposed. This is particularly advantageous when the clamp that is in the area of the electrical contacting and that is to be connected and/or the connecting cable are not sterilized and in particular are provided for multiple use. This is especially advantageous when monitoring central venous catheters.

The number of connecting contacts depends on the embodiment of the moisture sensor. For instance, the moisture sensor may include two connecting contacts between which the electrical resistance is measured. Two additional connecting contacts may be provided for connecting a terminating resistor. Instead of a connector tab with connecting contacts for a connecting piece of an electrical connecting line, however, it is also possible to run a connecting line out of the inventive device.

If the bottom layer is a composite material made of a textile material and a film, the desired flexibility of the layer may be adjusted by selecting a suitable film with an appropriate stiffness. The layer with the film will preferably impart adequate stability, but without losing the required flexibility.

The fastening means for detachably connecting the top and bottom layers may be embodied differently with respect to preventing a risk to the patient from the catheter slipping out. When there is a tensile load on the connecting cable for the moisture sensor, the fastening means for the tube covering should open so that the wrapping is withdrawn with the cable without exerting any appreciable tensile load on the tubing or connection system. Similarly, no appreciable tensile load should be exerted when there is a tensile load on the tube covering that may include a moisture sensor.

One preferred embodiment provides on the top side of the bottom layer and/or on the bottom side of the top layer a surface provided with an adhesive or adhesion coating, preferably a strip provided with an adhesive or adhesion coating for reversibly and repeatedly joining the top layer and the bottom layer.

One particularly preferred embodiment provides as fastening means a hook and loop closure or a plurality of hook and loop closures. Each hook and loop closures has two elements that may be detachably joined to one another. While the one element has a loop layer, the other element has a hook layer that when pressed reversibly hooks onto the loop layer. The two elements of the hook and loop closure are preferably strips.

One alternative embodiment provides that the fastening means have at least one tab provided on the top layer for inserting into a cut-out provided in the bottom layer. The tab may also be provided on the bottom layer and the cut-out in the top layer, however.

In another alternative embodiment, the tube covering has at least one press button that has a closure part with a button provided on the top layer and has a closure part with a depression provided on the bottom layer, it being possible to snap the button into place in the depression. The closure part with the button may also be provided on the bottom layer and the closure part with the depression may be provided on the top layer. The button and/or the depression for the press button may be produced by deep-drawing the top and bottom layers.

In another alternative embodiment, the fastening means have at least one fold provided on the bottom layer for clamping the top layer or at least one fold provided on the top layer for clamping the bottom layer. When there is adequate flexibility for the layers, this embodiment requires a certain stiffness, in particular of the top layer, which is preferably snapped and clamped into the fold. The required stiffness may be adjusted in the composite material made of textile material and film by the selection of suitable materials.

For fixing the tubing, in a particularly preferred embodiment the top layer and/or bottom layer have at least one notch for accommodating one segment of the tubing. The notch advantageously has a slit for introducing the tubing, a cut-out for clamping and holding a section of the tubing being connected thereto. One alternative embodiment provides an inserted part that has at least one clamping element for attaching one section of the tubing by clamping.

The tube covering may include the tubing from different tubing systems together with the associated connection systems, for instance the tubing and connection systems of single lumen catheters, double lumen catheters, or Tesio catheters. One or two tubings or connection systems may be accommodated in one wrapping.

One embodiment provides that the tube covering has a first rectangular wrapping and a second rectangular wrapping, the first wrapping and the second wrapping being connected to one another with a connecting tab. The connecting tab itself is advantageously a composite element made of a textile material and a film. The connecting tab preferably has greater flexibility than the wrapping, which again may be adjusted by selecting a suitable film.

Different embodiments of the present invention are explained in greater detail in the following using the drawings.

BRIEF DESCRIPTION OF THE DRAWINGS

FIGS. 3A through 3C are simplified schematic depictions of an alternative embodiment of the sterile tube covering that has a moisture sensor.

FIGS. 6A through 6C depict another exemplary embodiment of the tube covering.

FIG. 9 depicts another exemplary embodiment of the tube covering.

FIG. 10 depicts another exemplary embodiment of the tube covering.

DETAILED DESCRIPTION

A superior aspect of the present invention is the protection of connection systems, especially luer lock connection systems, for connecting tubing, especially tubing for a central venous catheter for acute dialysis, from penetration by microbes, especially from droplet infection.

Figure 1A:
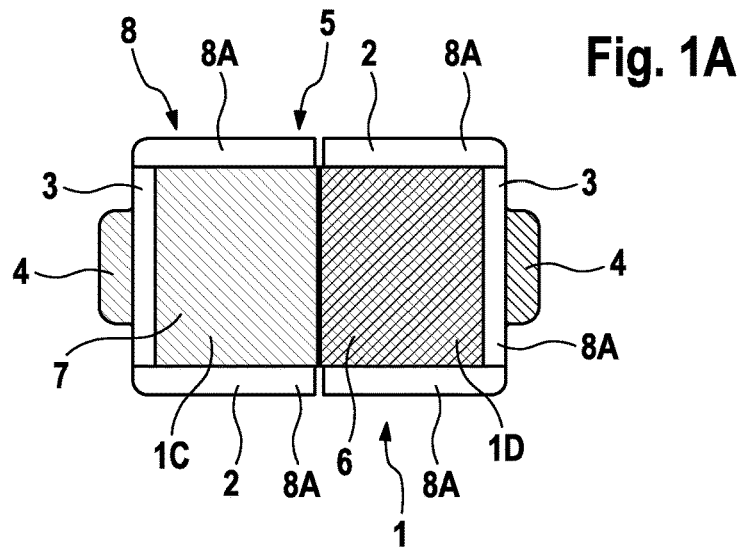
FIG. 1A is a simplified schematic top view of a first embodiment of the open sterile tube covering.
Figure 1B:
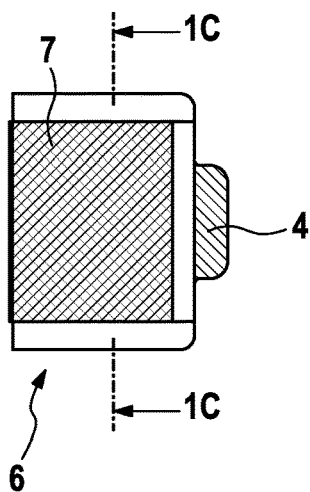
FIG. 1B is a top view of the folded tube covering from FIG. 1A.

FIGS. 1A and 1B depict one exemplary embodiment of the inventive tube covering, which is intended in particular for a central venous catheter in acute or chronic dialysis. The sterile tube covering is produced from a single material piece 1 that is cut from a material sheet or is produced from a material piece created by combining component pieces, the component pieces having each been cut from a material sheet. The material piece 1 is a composite material made of an absorbent material 1A, especially a textile material, for instance a woven fabric, and a film 1B that is not permeable for fluid. The film 1B is disposed on the exterior side and the woven fabric 1A is disposed on the interior side of the folded covering.

In the present exemplary embodiment, the material piece 1 is cut essentially in a rectangle. In FIGS. 1A and 1B the long sides are labeled 2 and the narrow sides are labeled 3. There is a handle tab 4 on each of the narrow sides 3 of the material that has been cut. The handle tabs 4 on the narrow sides 3 are usefully offset to one another such that the tube covering is easy to open, even with disposable medical gloves.

The essentially rectangular material piece 1 is folded such that the bottom side of the one half 1C rests on the top side of the other half 1D (single fold). This creates an openable wrapping 5 with a bottom layer 6 on which a luer lock connector may be placed and a top layer 7 for covering the luer lock connector, which together with the associated tubing segment may be placed into the wrapping. The wrapping is dimensioned such that the wrapping may enclose two luer lock connectors with the associated tubing segments.

Fastening means 8, which may in principle be embodied differently, are provided for joining the top layer 7 and the bottom layer 6 or for closing the wrapping 5. In the present exemplary embodiment, the fastening means 8 are surfaces 8A that are provided on the top and/or bottom layers and that are provided with an adhesive or adhesion layer. The surfaces 8A are preferably strips that run along the long and narrow sides 2, 3 on the edges of the material piece so that the wrapping 5 may be closed completely. The adhesive or adhesion strips 8A are embodied such that the wrapping may be securely closed and also easily opened.

The tubing can simply lead out of the wrapping 5 at different points so that the wrapping can adapt to the course of the tubing. The wrapping is closed with the adhesive or adhesion strips 8A at the passages for the tubes, the top and/or bottom layers 7, 6 being positioned close against the tubes so that the risk of microbes penetrating is minor. Thus there is no need to cover the luer lock connectors with a sterile cloth and protection is further enhanced.

One particular aspect of the present invention lies in monitoring the luer lock connectors for the central venous catheter for escaping blood.

Figure 1C:
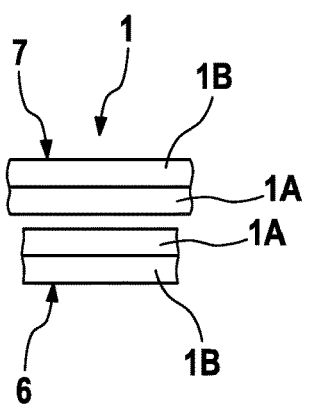
FIG. 1C is a section through the folded tube covering from FIG. 1C.

In the described exemplary embodiment referenced in FIGS. 1A through 1C, the film 1B of the composite material is a transparent film that permits continuous visual control so that it is possible to immediately detect whether blood has escaped from the luer lock connector. The film preferably comprises LDPE (low density polyethylene). The absorbent material 1A of the composite material preferably has a light color—the absorbent material is in particular a white woven fabric—so that blood absorbed by the woven fabric is easily detected through the transparent film 1B.

However, if the inventive tube covering alone is to provide the protection for the luer lock connector, the film 1B may also be a non-transparent film that is not permeable for fluid. A transparent film may also be provided only on the top layer 7.

The following shall describe various exemplary embodiments of the inventive tube covering that permit the escape of blood to be detected with a moisture sensor. The embodiments are connected to a device for monitoring a vascular access, which device may be a component of a blood treatment device.

Figure 2:
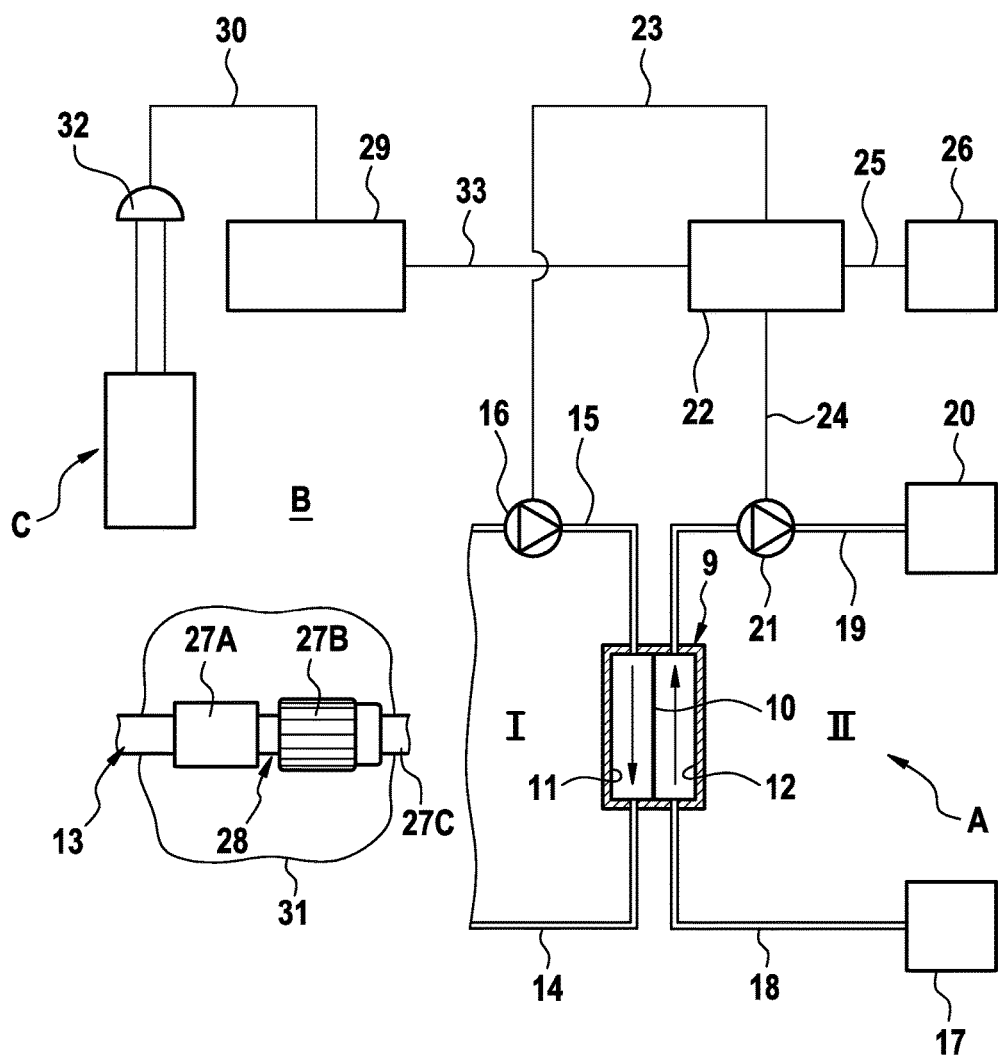
FIG. 2 depicts the essential components of a blood treatment device that has a device for monitoring a vascular access.

FIG. 2 depicts the essential components of a blood treatment device, especially a hemodialysis device A for acute or chronic dialysis, which has a device B for monitoring a vascular access, in particular a vascular access having a central venous catheter. In the present exemplary embodiment, the monitoring device B is a component of the hemodialysis device A. First the dialysis device shall be described.

The hemodialysis device A has a dialyzer 9 that is divided into a blood chamber 11 and a dialysis fluid chamber by a semipermeable membrane 10. Vascular access to the patient is provided with a central venous catheter 13 that is connected to the neck of the patient. The central venous catheter 13 is part of the extracorporeal blood flow I (only part of which is shown) that includes the blood chamber 11 of the dialyzer 9 and tubing 14, 15. A blood pump 16 is provided for moving the blood in the extracorporeal flow.

The dialysis fluid flow II in the dialysis device A includes a dialysis fluid source 17 to which a dialysis fluid supply line 18 is connected that leads to the inlet of the dialysis fluid chamber 12 in the dialyzer 9. A dialysis fluid discharge line 19 goes out from the outlet of the dialysis fluid chamber 12 in the dialyzer 9 and leads to an outlet 20. A dialysis fluid pump 21 is interposed in the dialysis fluid discharge line 19.

The dialysis device is controlled by a central control unit 22 that actuates the blood and dialysis fluid pumps 16, 21 via control lines 23, 24. The central control unit 22 is connected via a data line 25 to an alarm unit 26 that provides a visual and/or acoustic and/or tactile alarm if there is a fault.

In the present exemplary embodiment, the monitoring device B, depicted only schematically, monitors a luer lock connector 28 with the connecting parts 27A and 27B for connecting the central venous catheter 13 to tubing 27C that is connected to the extracorporeal blood flow I.

The monitoring device B has an evaluation unit 29 that is connected via a connecting line 30 to the inventive tube covering C, which is arranged at the tube connection point 31. The connecting line 30 is connected by an electrical connecting piece 32 to the connecting contacts (not shown in FIG. 2) of a moisture sensor (also not shown in FIG. 2) that is disposed in the tube covering C.

The evaluation unit 29 is connected to the central control unit 22 of the dialysis device A via a data line 33. If blood escapes from the tube connection point 31, the evaluation unit 29 in the monitoring device B generates a control signal that the central control unit 22 receives that intervenes in the blood treatment. The central control unit 22 stops the blood pump 16 and generates an alarm signal so that the alarm unit 26 provides an acoustic and/or visual and/or tactile alarm.

The exemplary embodiments of the inventive tube covering described in the following are distinguished from the embodiment described with reference to FIGS. 1A through 1C essentially in that a moisture sensor 34 is embedded in the absorbent material 1A and is attached to the monitoring device B. Equivalent parts are given the same reference number in the figures.

FIGS. 3A through 3C depict a first exemplary embodiment of a tube covering C having moisture sensor 34.

The tube covering is produced from a single material piece or from one material piece 1 made of two component pieces that have been combined, the single material piece or the two component pieces each being cut from a material sheet that is a composite made of an absorbent woven fabric 1A and a film 1B that is not permeable to fluid. The film 1B is disposed on the exterior side and the woven fabric 1A on the interior side of the foldable covering. The film and the woven fabric may comprise individual sections having different material properties.

In the present exemplary embodiment, the material piece 1 has a first section cut essentially in a rectangle that is folded such that the bottom side of the one half 1C lies on the top side of the other half 1D (single fold). As in the embodiment in FIGS. 1A through 1C, this creates an openable wrapping 5 having a bottom layer 6 onto which a luer lock connector may be placed and a top layer 7 for covering the luer lock connector, which may be placed into the wrapping together with the associated tubing section.

The material piece 1 moreover has a second, longitudinally extended section that acts as a connector tab 35 that in the present exemplary embodiment is connected to the bottom layer 6, but may also be attached to the top layer 7. The electrical contacting with the connecting piece 32 for the monitoring device B is at the end of the connector tab.

In the present invention, the detachable fastening means 8 for connecting the top layer 7 and the bottom layer 6 or for closing the wrapping 5 have a fastening tab 8B provided on the exterior side of the top layer and a cut-out 8C provided on the exterior side of the bottom layer 6. The tab 8A is provided with lateral slits 8D and the cut-out 1C with lateral undercuts 8E so that the tab is permanently attached and may be secured in and easily removed from the cut-out. A slit may also be provided instead of a cut-out.

Disposed on the exterior side of the bottom layer 6 below the cut-out 8C for receiving the fastening tab 8B is a handle tab 4 for opening the covering.

FIG. 3B depicts the luer lock connectors 27 that are adjacent to one another between top and bottom layers 7, 6 and that are enclosed by the wrapping 5.

The moisture sensor 34 is embedded in the absorbent woven fabric 1A of the composite material that comprises electrically conducting and electrically non-conducting warp and weft threads. The non-conducting warp threads and non-conducting weft threads as well as the conducting warp threads and the conducting weft threads are arranged such that embodied in the woven fabric 1A is an electrically conducting structure that forms the moisture sensor 34. WO 2011/116943 describes such a woven fabric with an electrically conducting structure in detail and is explicitly referenced.

FIG. 3C depicts the conductor segments 34A, 34B of the electrically conducting structure, which are perpendicular to one another. The intersection points 34 C at which the warp and weft threads running perpendicular to one another make electrical contact in the woven fabric are circled. Some of the conductor segments 34A, 34B lead to the end of the connector tab 35, the connecting contacts 35A for the connecting piece 32 (FIG. 2) in the monitoring device B being embodied at the ends of the conductor segments 34B.

The film 1B of the composite material may impart to the material an adequate stiffness that the woven fabric 1A alone does not have. If the film 1B comprises a plurality of segments of different stiffness, individual segments of the wrapping 5 may also have different flexibility. The connector tab 35 preferably has greater flexibility, the film 1B being stiffer and/or thicker in the area of the connector tab than in the area of the essentially rectangular segment, in which the film is thinner and/or more flexible.

In the present exemplary embodiment, the film 1B is lined with the woven fabric 1A. The composite material made of film and woven fabric is thermally deformed such that the wrapping 5 is pre-stressed into the folded condition. When the wrapping 5 is opened, the composite material made of film and woven fabric is elastically deformed against the pre-stress, especially in the area of the fold 36. Notches with which the restoring force may be adjusted may be provided in the area of the fold 36.

The luer lock connectors 27 and the associated tubing 27C may be adequately fixed in the wrapping 5 solely by the pre-stress of the top and bottom layers 7, 6. However, one preferred embodiment provides additional fixation of the tubing 27C in the wrapping 5. For fixing the tubing, notches 37 are provided in the bottom layer 6 that are preferably arranged on both sides of the connector tab 35. They each have a slit 37A into which the tubing section 27A may be laterally inserted. Connected to the slit 37A is a cut-out 37B for receiving the tubing section 27C, which may be fixed into the cut-out by clamping. The notches 37 may also be provided on the top layer 7, however.

The arrangement of the notches 37 on both sides of the connector tab 35 has the advantage that the slits 37A may be opened easily by lifting the connector tab 35, which facilitates insertion of the tubing.

Figure 4A:
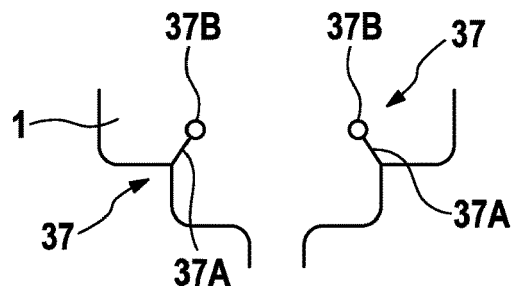
FIGS. 4A through 4F depict different embodiments of notches in the top and bottom layers of the tube covering for fixing the tubing by clamping.
Figure 4B:
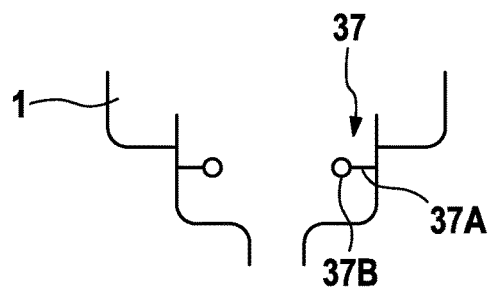
Figure 4C:
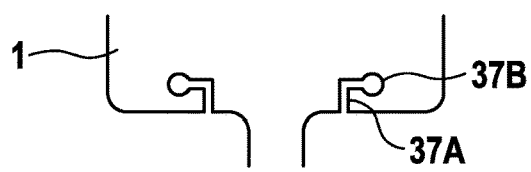
Figure 4D:
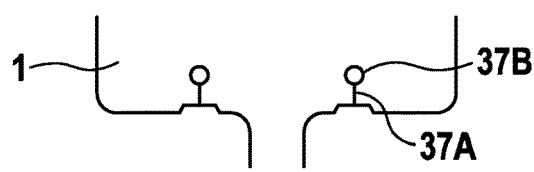
Figure 4E:
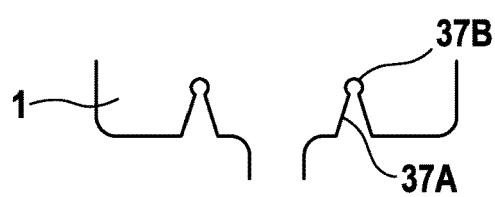
Figure 4F:
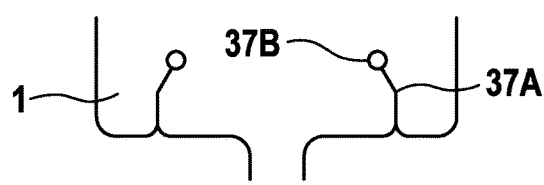

FIGS. 4A through 4F depict different embodiments for the notches 37 on the wrapping 5. FIG. 4A depicts one embodiment in which the slits 37A are arranged at an angle to the lower lateral edge of the bottom layer 6. This ensures both that the tubing 27A is securely held and that it is easy to insert. FIG. 4B depicts an embodiment in which the notches 37A run parallel to the lower lateral edge of the bottom layer, facilitating simple insertion of the tubing. FIG. 4C depicts an embodiment with a slit 37A that has two sections at right angles to one another. The width of this slit is greater than that of the other slits and forms an insertion channel into which the tubing may be easily placed and which provides a secure hold. FIG. 4D depicts the embodiment as in the embodiment shown in FIGS. 3A through 3C. FIG. 4E depicts an embodiment having slits 37A that open widely to the lower lateral edge so that it is particularly easy to insert the tubing. FIG. 4F depicts an embodiment in which the slits 37A have a section that is perpendicular to the lower lateral edge and a section that runs at an angle to the lateral edge so that it is easy to insert the tubing and a secure hold is ensured.

In the embodiments in FIGS. 4A through 4F, connected to the slit 37A are cut-outs 37B that are preferably circular. The diameter of the cut-outs is dimensioned such that the tubing 27C is held by clamping.

Figure 5:
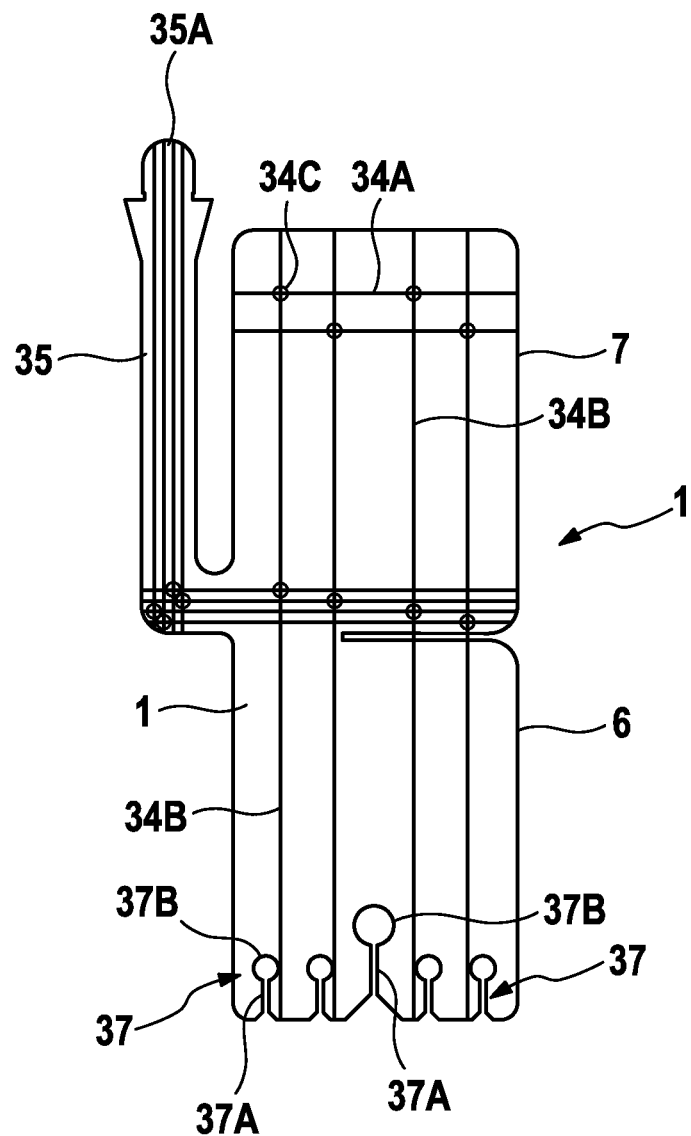
FIG. 5A depicts another exemplary embodiment of the tube covering.

FIG. 5 depicts another embodiment of the inventive tube covering. The tube covering in FIG. 5 is distinguished from the tube covering in FIGS. 3A through 3C by the different arrangement of the conductors 34A, 34, B and the different design of the connector tab 35 and notches 37 for receiving the tubing, as well as by the shape and dimensions. Equivalent parts again have the same reference numbers. The connector tab 35 for the embodiment in FIG. 5 is joined to the top layer 7 and extends parallel to the long side of the top layer beyond the top layer, the connector tab being attached to the top layer in the area where the top and bottom layers 7, 6 are joined.

On the bottom layer 6 the tube covering has notches 37 that are for receiving the tubings and that are embodied differently. The notches 37 are distinguished from one another by the diameter of the circular cut-outs 37B. However, the notches depicted in FIGS. 4A through 4F may also be provided.

The different design of the notches 37 permits different blood tube systems to be fixed by clamping; these include for instance single lumen and double lumen catheters. The notches 37 are embodied such that the tube covering may be detached from the blood tube system with a greater tractive force.

The material piece 1 for the tube covering may in principle comprise different materials in the area where the top and bottom layers 7, 6 are connected. The selection of suitable materials may be used to determine whether the top and bottom layers 7, 6 are resiliently pre-stressed in the folded position for the tube covering. The resilient pre-stress is determined by the material properties.

FIGS. 6A through 6C depict another embodiment of the inventive tube covering that has two wrappings 5, each of which may receive one or two connection systems together with the associated tubing sections. The design of the two wrappings 5, each of which has a top and a bottom layer 7, 6, is the same as for the wrapping from FIGS. 3A through 3C. Equivalent parts are again provided with the same reference number.

The first and second wrappings 5 are connected to one another with a connecting tab 38, the ends of which are attached to the opposing narrow sides of the wrappings.

The tube covering again comprises a material piece 1 that is a composite material made of an absorbent material 1A and a film 1B. In the area of the connecting tab 38, preferably a film 1B that has a lower stiffness is lined with the absorbent material 1A, than in the area of the wrappings 5, so that the connecting tab 38 is more flexible than the wrappings 5. This ensures that the wrappings can adapt in the alignment to the course of the tubings 27A. FIG. 6B depicts the course of the tubings 27A, the connection systems for the tubing not being shown in FIG. 6B. FIG. 6C depicts the conductors 34A, 34B for the moisture sensor 34.

Figures FIG. 7A through 7D depict another embodiment of the inventive tube covering. The tube covering for FIGS.

Figure 7A:
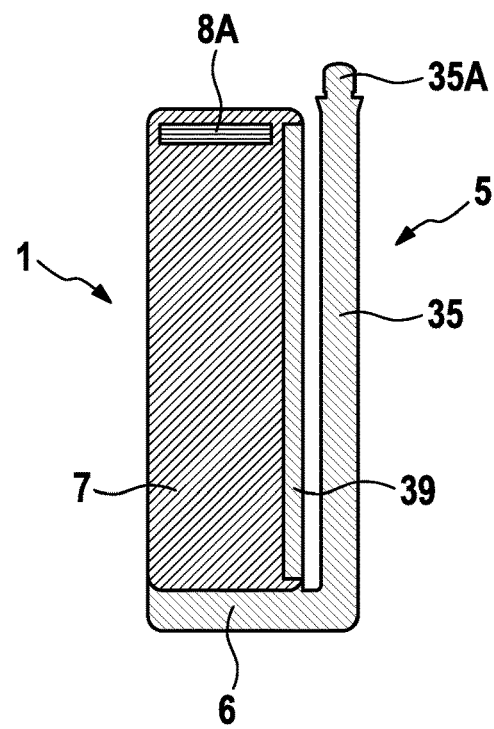
FIGS. 7A through 7E depict another exemplary embodiment of the tube covering.
Figure 7B:
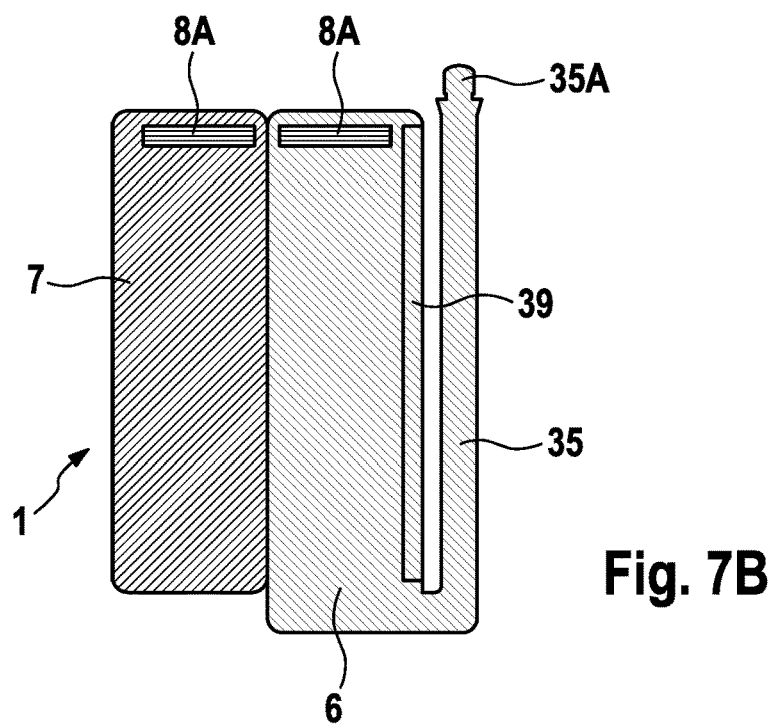
Figure 7C:
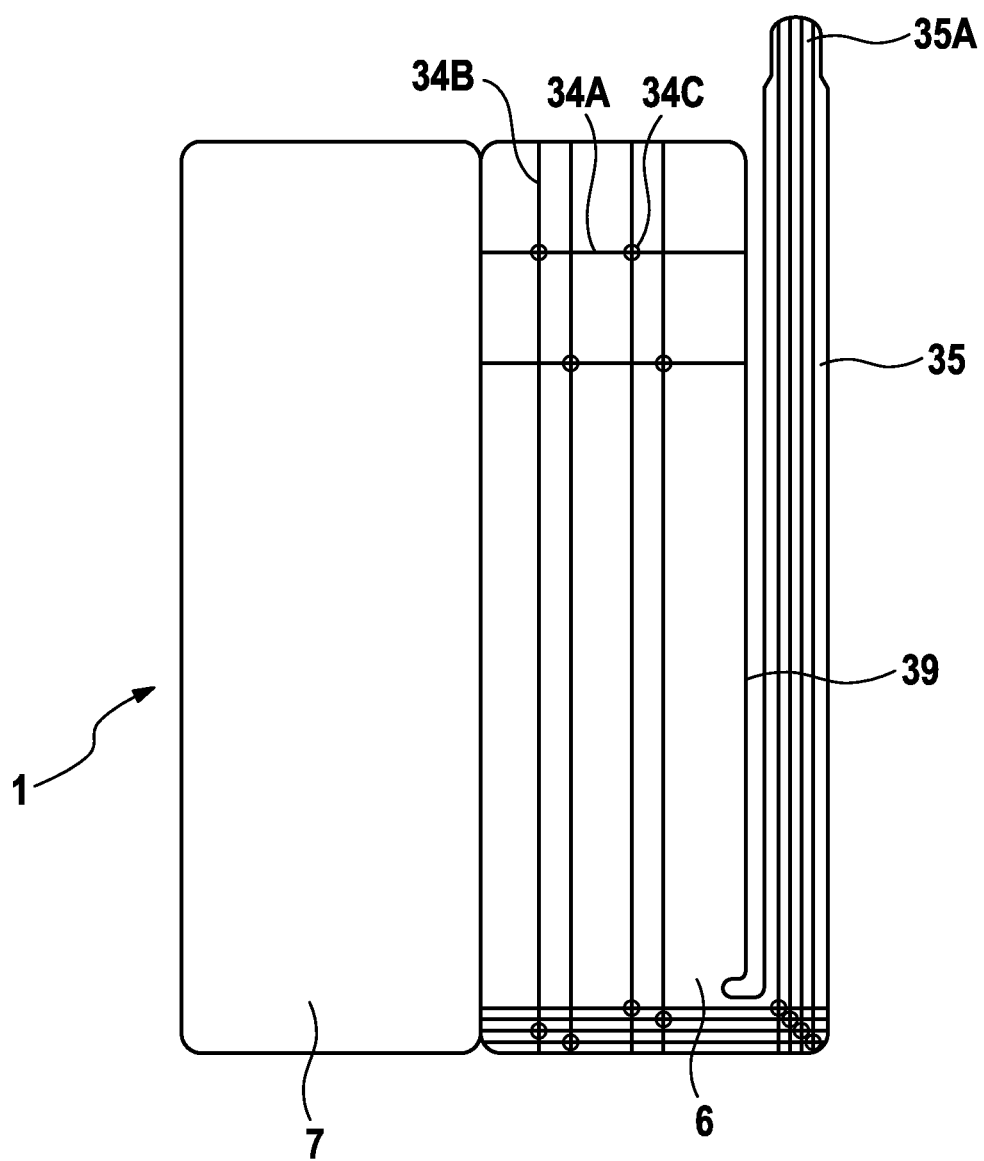
Figure 7D:
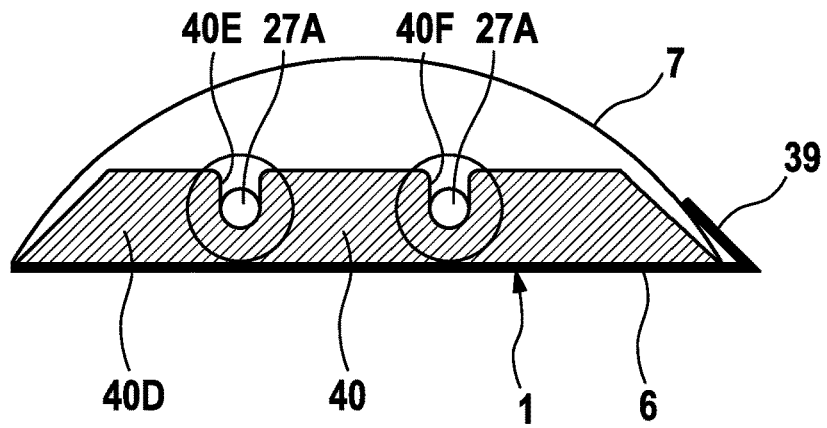

7A through 7D does not have a fastening tab on the top layer that is inserted into a cut-out on the bottom layer, but rather has a fold 39 provided on the bottom layer 6 for clamping the top layer 7. The fold 39 on the bottom layer 6 runs along its long edge. In the area of the fold 39 the material piece 1 has adequate stiffness for fixing the top layer 7 by clamping (FIG. 7D). The required clamping force is attained if the top layer 7 has adequate stiffness. The top layer is preferably wider than the bottom layer 6 so that the top layer 7 can curve outward and thus adequate space can be created for the tubing(s).

The wrapping 5 is closed on the narrow side with an adhesive or adhesion strip 8A that may be provided on one or both narrow sides of the top or bottom layer 7, 6. In the present exemplary embodiment, a hook and loop closure is provided on only one of the two narrow sides.

In the embodiment in FIGS. 7A through 7D, the two tubings 27A are fixed not by notches in the bottom layer, but by a inserted element 40 that preferably comprises plastic.

Figure 7E:
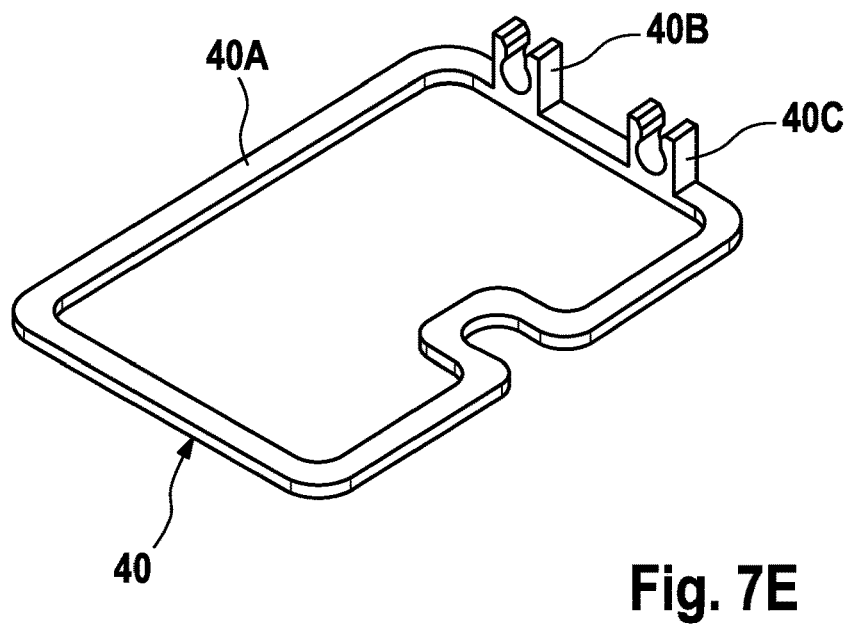

FIG. 7E is a perspective elevation of one exemplary embodiment of the inserted element 40. FIG. 7D is a sectional depiction of an alternative embodiment.

The inserted element 40 from FIG. 7E has a frame 40A with two clamps 40B, 40C arranged adjacent to one another in which the tubing sections 27A are held by clamping. The inserted element in FIG. 7D has a clamp 4D with two cut-outs 40E, 40F for receiving and clamping the two tubings 27A.

In the exemplary embodiment in FIGS. 7A through 7D the connector tab 35 extends parallel to the long side of the top layer 7 beyond the top layer.

Figure 8:
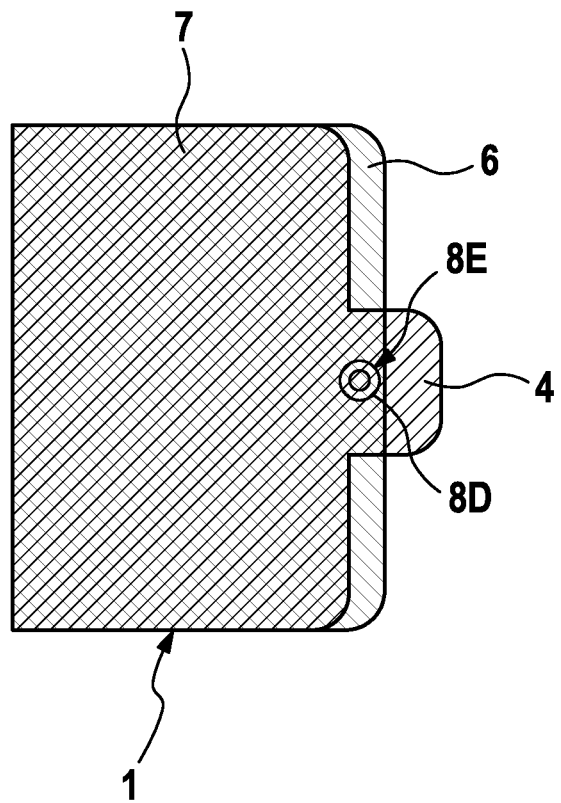
FIG. 8 depicts another exemplary embodiment of the tube covering.

FIG. 8 is a top view of another exemplary embodiment of the folded tube covering.

Provided in the top layer 7 the tube covering in FIG. 8 is a handle tab 4, and disposed on the bottom side thereof is a closure part 8D (suggested only in outlines) with a button that may be pressed and snapped into a depression 8E on the bottom layer 6. This creates a secure closure that is easy to open. The two closure parts for the press button may comprise metal or plastic and may be joined to the material piece 1. However, it is also possible to embody a button and a depression on the top or bottom layer using a permanent deformation (deep drawing) in the film 1B.

FIGS. 9 and 10 depict alternative embodiments of the tube covering that are not fashioned from an integral material piece but rather from two pieces that are joined together to create a single material piece. Equivalent parts are again provided with the same reference number.

The sterile tube covering in FIG. 9 is fashioned from a material piece 1 made of two combined component pieces 1', 1", the component pieces each being cut from one material sheet. The material sheet is a transparent film sheet, especially a film made of LDPE (low density polyethylene). The first component piece 1' forms the top layer 7 and the second component piece forms the bottom layer 6 of the wrapping. The two component pieces 1' 1" are joined to one another on one side. The two component pieces 1', 1" are preferably welded to one another on one side. However, they may also be glued to one another. The joining seam, especially a welding seam, has the reference number 41. In the present exemplary embodiment the two component pieces 1', 1" are cut essentially in rectangles.

In the present exemplary embodiment the joining means 8 for joining the top layer 7 and the bottom layer 6 or for closing the wrapping 5 are hook and loop closures, especially micro hook and loop closures, that each comprise two different strips 8', 8" that may be detachably joined to one another. The one strip 8' has a hook layer and the other strip 8" has a loop layer. The strips 8' with the hook layer are disposed on the top side of the bottom layer 6 and the strips 8" with the loop layer are disposed on the bottom side of the top layer 7. They run along the edges of the two layers 6, 7.

Applied to the top side of the bottom layer 6 is a material piece 1A made of an absorbent material that has the moisture sensor 34, only suggested in outline in FIG. 9, that was described in the foregoing and that is embodied as an electrically conducting structure. The absorbent material piece 1A extends to the strips of the hook and loop closure, the connector tab 35 extending outward beyond the bottom layer 6 on one side of the tube covering. Since the strips 8" of the hook and loop closure 8 with the loop layer are disposed on the bottom side of the top layer 7, the hook and loop closure strips cannot hook onto the absorbent material piece 1A.

FIG. 10 depicts an exemplary embodiment that is distinguished from the embodiment in FIG. 9 in that the absorbent material piece 1A does not have a moisture sensor. The absorbent material may be a hydrophilic non-woven fabric, which should be a low particle, sterilizable non-woven fabric.

The method for producing the tube coverings in FIGS. 9 and 10 shall be described in the following.

The strips 8" of the hook and loop closure 8 with the loop layer are applied to a first material sheet, in particular a film sheet, at a pre-specified distance from one another, while the strips 8' of the hook and loop closure 8 with the hook layer are applied to a second material sheet, especially a film sheet, at a pre-specified distance from one another. The hook and loop closure strips may be strips provided with an adhesive or adhesion layer that are glued to the film sheets.

Material pieces 1A made of an absorbent material that have a moisture sensor 34 (FIG. 9) or that do not have a moisture sensor (FIG. 10) are applied to a second material sheet, especially a film sheet, at a pre-specified distance from one another. Then the first component pieces 1' are separated from the first material sheet and the second component pieces 1" are separated from the second material sheet. Then the two component pieces 1', 1" are joined to one another to create a single material piece 1. The film pieces are preferably welded on one side. Then the individual material pieces 1 are folded such that the bottom side of the top layer 7 lies on the top side of the bottom layer 6. Then the individual tube coverings are sterilized and then packaged. However, they may also first be packaged and then the packages may be sterilized. It is also possible to package the open tube coverings.

The invention claimed is:

1. A sterile tube covering for a medical tubing system for monitoring the vascular access during extracorporeal blood treatment with which a fluid is at least one of supplied to a patient or removed from a patient via at least one tubing, the sterile tube covering comprising:

at least one flexible bottom layer on which at least one of a section of the at least one tubing or a connection system of the at least one tubing is placed, the at least one flexible bottom layer comprising an absorbent material configured to absorb a fluid escaping from at least one of the section of the at least one tubing or the connection system of the at least one tubing, the absorbent material having a moisture sensor that is embodied as an electrically conducting structure, the absorbent material comprising a woven fabric having conducting warp threads and conducting weft threads that are arranged such that the electrically conducting structure is embodied in the woven fabric, the at least one flexible bottom layer having a slit formed therein, the slit beginning at an edge of the at least one flexible bottom layer and extending to a cut-out formed in the at least one flexible bottom layer, the cut-out configured to receive the section of the at least one tubing;

at least one flexible top layer configured to cover at least one of the section of the at least one tubing or the connection system of the at least one tubing, wherein the bottom layer and the top layer are joined to one another such that they form an openable wrapping configured for insertion of the section of at least one of the section of the at least one tubing or the connection system of the at least one tubing; and a fastening device provided on the top layer and bottom layer, the fastening device configured to detachably join the top layer and the bottom layer.

2. The tube covering according to claim 1, wherein:
the top layer and the bottom layer form a single material piece, and
a bottom surface of the top layer lies on a top surface of the bottom layer when the wrapping is folded closed.

3. The tube covering according to claim 1, wherein:
the top layer and the bottom layer are separate components which form a material piece, and
a bottom surface of the top layer lies on a top surface of the bottom layer when the wrapping is folded closed.

4. The tube covering according to claim 1, wherein the bottom layer is a composite material, the composite material including an absorbent material and a film, wherein the film is arranged on an exterior side of the tube covering and the absorbent material is arranged on an interior side of the tube covering.

5. The tube covering according to claim 1, wherein the woven fabric of the absorbent material further comprises non-conducting warp threads and non-conducting weft threads.

6. The tube covering according to claim 1, wherein the tube covering further comprises:
connecting contacts configured to electrically contact the moisture sensor, the connecting contacts disposed at an end of a longitudinal section that is connected to the top layer or bottom layer.

7. The tube covering according to claim 1, wherein the top layer is a composite material, the composite material including an absorbent material and a film, wherein the film is arranged on an exterior side of the tube covering and the absorbent material is arranged on an interior side of the tube covering.

8. The tube covering according to claim 7, wherein the film is a transparent film such as LDPE.

9. The tube covering according to claim 1, wherein the fastening device has on at least one of a top surface of the bottom layer or on a bottom surface of the top layer at least one surface provided with an adhesive or adhesion layer such as a strip provided with the adhesive or the adhesion layer.

10. The tube covering according to claim 1, wherein the fastening device has at least one fastening tab provided on the top layer configured for insertion into a tab-receiving cut-out provided in the bottom layer.

11. The tube covering according to claim 1, wherein the fastening device has at least one first closure part with a button provided on the top layer and a second closure part with a depression provided on the bottom layer such that the button is configured to snap into place in the depression.

12. The tube covering according to claim 1, wherein the fastening device has a fold provided on the bottom layer configured to receive and clamp the top layer.

13. The tube covering according to claim 1, wherein the at least one flexible bottom layer has a second slit formed therein, the second slit beginning at an edge of the at least one flexible bottom layer and extending to a second cut-out formed in the at least one flexible bottom layer, the second cut-out being configured to receive a section of a respective tubing.

14. The tube covering according to claim 1, wherein the at least one flexible bottom layer has at least one tab-receiving cut-out formed therein and configured to receive a fastening tab.

15. The tube covering according to claim 1, wherein the at least one tubing has an insert element having at least one clamp configured to attach the section of the at least one tubing by clamping.

16. The tube covering according to claim 1, further comprising:
a first wrapper and a second wrapper, the first wrapper and the second wrapper configured to join to one another with a connecting tab.

17. The tube covering according to claim 16, wherein the connecting tab is a composite material made of a textile material and a film.

18. A method for producing a sterile tube covering for a medical tubing system, the tube covering having at least one flexible bottom layer on which at least one of a section of the at least one tubing or a connection system of the at least one tubing is placed, and having a flexible top layer for covering at least one of the section of the at least one tubing or the connection system of the at least one tubing, the method comprising:
providing a first material sheet for cutting first component pieces for the top layer;
providing a second material sheet for cutting second component pieces for the bottom layer;
applying material pieces made of an absorbent material to the second material sheet at a predetermined distance from one another to form a bottom layer material comprising an absorbent material configured to absorb a fluid escaping from at least one of the section of the at least one tubing or the connection system of the at least one tubing, the absorbent material having a moisture sensor that is embodied as an electrically conducting structure, the absorbent material comprising a woven fabric having conducting warp threads and conducting weft threads that are arranged such that the electrically conducting structure is embodied in the woven fabric;
applying first fastening devices to the first material sheet at a predetermined distance from one another;
applying second fastening devices to the second material sheet at a predetermined distance from one another;
separating the first component pieces from the first material sheet and separating the second component pieces from the second material sheet;
forming a slit in a second component piece of the second component pieces, the slit beginning at an edge of the second component piece;
forming a cut-out in the second component piece, the cut-out configured to receive a section of tubing, the slit extending from the edge to the cut-out; and
joining the first and second component pieces to form a single material piece.

19. The method according to claim 18, wherein the first and second fastening devices together comprise a hook and loop closure.

20. The method according to claim 18, wherein the first and second material sheets are film sheets, wherein the first and second component pieces are welded to one another on one side.

21. The method according to claim 18, wherein the material pieces are folded such that a bottom surface of the top layer lies on a top surface of the bottom layer.

22. The method according to claim 18, wherein one of:
  individual tube coverings are first sterilized and then packaged; or
  individual tube coverings are first packaged and then sterilized.

* * * * *